United States Patent [19]

Braus et al.

[11] 4,332,957
[45] Jun. 1, 1982

[54] PHENOXYALKOXY SILANES

[75] Inventors: Harry Braus; Anthony Barlow; Melvin F. Maringer, all of Cincinnati, Ohio

[73] Assignee: National Distillers & Chemical Corp., New York, N.Y.

[21] Appl. No.: 219,012

[22] Filed: Dec. 22, 1980

[51] Int. Cl.$^3$ .............................. C07F 7/04; C07F 7/18
[52] U.S. Cl. ...................................... 556/446; 556/471
[58] Field of Search ........................................ 556/446

[56] References Cited

U.S. PATENT DOCUMENTS

| | | | |
|---|---|---|---|
| 2,559,342 | 7/1951 | Burkhard | 556/446 |
| 2,851,471 | 9/1958 | Pines et al. | 556/446 |
| 3,048,499 | 8/1962 | Jellinek | 556/446 X |
| 3,522,284 | 7/1970 | Kötzsch | 556/471 |
| 3,814,691 | 6/1974 | Csejka et al. | 556/446 X |
| 4,060,538 | 11/1977 | Kötzsch et al. | 556/471 X |
| 4,141,851 | 2/1979 | Askew et al. | 556/446 X |

Primary Examiner—Paul F. Shaver

Attorney, Agent, or Firm—Kenneth D. Tremain

[57] ABSTRACT

Compositions of matter described as alkyl or alkenyl tris or tetrakis (phenoxyalkoxy) silanes are useful as tree retardant additives for polymeric insulation compositions. These silanes have the general formula:

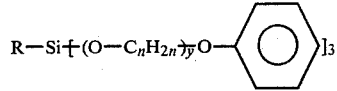

wherein R is $C_1$-$C_5$ alkyl, $C_2$-$C_4$ alkenyl or

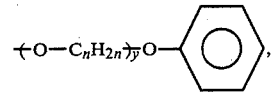

y is an integer of 1 to 5 and n is an integer of 1 to 4.

14 Claims, No Drawings

PHENOXYALKOXY SILANES

BACKGROUND OF THE INVENTION

1. Field of the Invention

This invention relates to silane monomers. More particularly, it relates to phenoxyalkoxy-substituted silanes. This invention especially relates to alkyl or alkenyl tris (phenoxyalkoxy) silanes and tetrakisphenoxyalkoxy silanes.

2. Background of the Invention

Organo silanes have found wide use as lubricants, hydraulic fluids, coupling agents in mineral filled polymeric compositions, water repellants, tree retardant additives for polymeric electrical insulation and intermediates in preparing organopolysiloxanes.

U.S. Pat. No. 2,559,342 of Burkhard discloses a family of hydrocarbyl alkoxyethoxy silanes prepared by reacting organochlorosilanes with alkoxyethanols. U.S. Pat. No. 3,814,691 of Csejka et al utilizes organo silanes as a hydraulic fluid base stock. These silanes have the general formula:

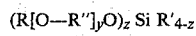

$$(R[O{-}R'']_yO)_z\, Si\, R'_{4-z}$$

wherein R is a $C_1$–$C_{10}$ alkyl or a $C_6$–$C_{10}$ aryl group, R' is a $C_1$–$C_4$ alkyl group, R" is a $C_2$–$C_4$ alkylene group, y is 1 to 5 and z is 1 to 3. Only nine compounds of the above formula are specifically enumerated and of these only two exemplify a compound where a single alkylene group is present and in both cases the silane is dimethyl. None of the silanes disclosed in U.S. Pat. Nos. 3,048,499 of Jellinek and 2,851,474 of Pines et al. contains an aryl group while all of the organic groups are aryl in the silanes of British Pat. No. 953,421. In U.S. Pat. No. 4,141,851 of Askew et al the most pertinent version of the broad general formula requires two Si-C bonds and two Si-O-C bonds on the single Si atom.

The procedure employed in the Burkhard patent to prepare the organosilanes disclosed therein involves reacting an organochlorosilane with a 2-alkoxyethanol under reflux conditions until HCl evolution is completed. Csejka et al teaches that silanes of this patent are made by reacting an alkyl-halo-silane with polyalkylene glycol monoalkyl or monoaryl ethers in an inert medium.

Copending U.S. patent application Ser. No. 161,932 discloses the addition of organo silanes to polymeric compositions to provide increased resistance to the phenomena known as electrical treeing and water treeing, said compositions being useful as insulation for electrical cables.

Polymeric compositions are well-known and are used extensively as insulation materials for wire and cable. As an insulator, it is important that the composition have various physical and electrical properties, such as resistance to mechanical cut-through, stress crack resistance and dielectric failure. Recent publications have indicated that water tree growth and electrical tree growth in the insulation are particularly important problems since they are associated with, though not necessarily totally responsible for, dielectric failure. The term "tree" has been applied to this type of insulation breakdown since the area of failure is a void space having the appearance of a tree in profile, i.e., the shape of a tree trunk and its upper foliage. Treeing usually is a slowly developing phenomenon and may take years to cause a failure in the insulation.

An important application for an insulation material is in high voltage transmission and distribution cable, especially in direct buried underground service. Two types of trees have been observed in these power cables, to wit, electrical trees and water trees, which are sometimes referred to as electrochemical trees. It is generally believed that electrical trees and generated by corona discharges caushing fusion and breakdown of the polymer, whereas water trees are usually observed in cables buried in wet locations and have a different appearance compared to the electrical trees. Metal ions are usually found in water trees.

U.S. Pat. No. 4,144,202 of Ashcraft et al. relates to inhibiting the electrical breakdown of insulation by water treeing in dielectric materials based on ethylene polymers. As disclosed in the patent, water treeing is inhibited in the ethylene polymer compositions by employing therein organo silane compounds having an epoxy containing radical. German Offenlegungsschrift No. 2,737,430 discloses that certain alkoxysilanes added to polyolefin insulation prevent water-tree formation. Commonly assigned and copending U.S. patent application Ser. No. 161,932, filed June 23, 1980 discloses a number of organosilanes useful as tree retardant additives. Those particularly preferred contain at least one —$OC_2H_4$—O—R group where R is alkyl or aryl. Vinyl-tris (2-phenoxyethoxy) silane is specifically disclosed and exemplified as a useful water tree and electrical tree retardant for polymeric insulation.

It is an object of this invention to provide alkyl or alkenyl tris (phenoxyalkoxy) silanes or tetrakis phenoxyalkoxy silanes.

It is another object of this invention to provide organosilanes useful as water tree and electrical tree retardants.

SUMMARY OF THE INVENTION

In accordance with the present invention, there are provided compositions of matter which find particular utility as water tree and electrical tree retardant additives. Two particularly preferred compounds of the compositions of matter of this invention are methyl tris (2-phenoxyethoxy) silane and vinyl tris (2-phenoxyethoxy) silane. The compositions of matter of this invention correspond to the general formula

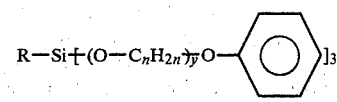

wherein R is $C_1$–$C_5$ alkyl, $C_1$–$C_4$ alkenyl or

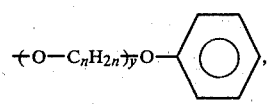

y is an integer of 1 to 5 and n is an integer of 1 to 4.

This invention is also concerned with the process for preparing these compositions of matter. This process is described as a process for preparing an organosilane corresponding to the formula:

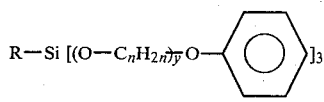

wherein R is $C_1$-$C_5$ alkyl, $C_2$-$C_4$ alkenyl or

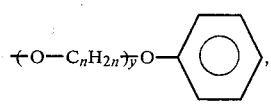

y is an integer of 1 to 5 and n is an integer of 1 to 4 which comprises:

(a) reacting together an alcohol having the formula:

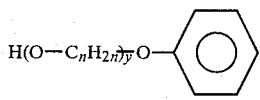

with a halosilane having the formula ($C_1$-$C_5$ alkyl) Si $X_3$ when R is $C_1$-$C_5$ alkyl, ($C_2$-$C_4$ alkenyl) Si $X_3$ when R is $C_2$-$C_4$ alkenyl or Si $X_4$ when R is

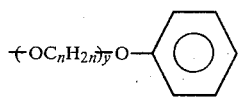

wherein X is a halogen and n and y have the meanings given above in the presence of a hydrogen halide acceptor and an inert solvent, (b) separating the hydrogen halide acceptor containing hydrogen halide from the reaction mixture, (c) isolating a compound having the formula

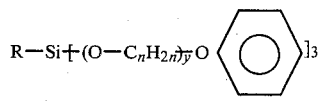

from the reaction mixture.

DESCRIPTION OF THE PREFERRED EMBODIMENTS

The present invention relates to a family of tris or tetrakis (phenoxyalkoxy) silanes and their method of preparation. Briefly, these silanes are described as $C_1$-$C_5$ alkyl or $C_2$-$C_4$ alkenyl tris or tetrakis (phenoxyalkoxy) silanes, particularly tris (2-phenoxyethoxy) silanes. Phenoxypolyalkoxy silanes are also included in the silanes of this invention.

In the general formula employed herein to depict these silanes, R may be, for example, an alkyl, such as, methyl, ethyl, propyl, isopropyl, butyl, isobutyl, amyl and the like or an alkenyl, such as vinyl, 1-methyl vinyl, allyl, butenyl-1, 2 or 3 and the like. Since the subscript on the $C_nH_{2n}$ radical can range from 1 to 4, $CH_2$, —$CH_2$—$CH_2$—, —$CH_2$—$CH(CH_3)$—, —$CH_2$—$CH_2$—$CH_2$—, —$CH_2$—$CH_2$—$CH(CH_3)$—, or —$CH_2$—$CH_2$—$CH_2$—$CH_2$— may comprise this portion of the formula. In the tetrakis silanes of the invention R is a phenoxyalkoxy radical as described hereinbelow. Although the two silane species listed above, methyl tris (2-phenoxyethoxy) silane and vinyl tris (2-phenoxyethoxy) silane, are relatively easy to prepare and thus are the preferred compounds, other examples of the compositions of this invention include ethyl tris (phenoxymethoxy) silane, vinyl tris (3-phenoxypropoxy) silane, propyl tris (4-phenoxybutoxy) silane, methyl tris (1-methyl-2 phenoxyethoxy) silane, allyl tris (1-methyl-3 phenoxypropoxy) silane, tetrakis (2-phenoxyethoxy) silane and the like as well as phenoxypolyalkoxy silanes such as, vinyl tris (phenoxyethoxyethoxy) silane, vinyl tris (phenoxytriethoxy) silane and the like.

The silanes of this invention have a variety of uses, such as, coupling agents in mineral filled polymeric compositions, water tree and electrical tree retardant additives in polymeric electrical insulation, intermediates for preparing organopolysiloxanes and other uses in which similar silanes have been employed.

The instant silanes may be prepared by reacting an organotrihalosilane or tetrahalosilane with a phenoxy-$C_1$-$C_4$ alkanol. This may be accomplished by combining the reactants in an inert organic solvent, such as, toluene, xylene and the like and heating the mixture under reflux until hydrogen halide evolution is completed. The desired silane may then be removed by distillation, e.g. vacuum distillation. In one particularly effective embodiment, a hydrogen halide acceptor, such as pyridine, dimethylaniline and the like is added to the reaction mixture to remove the hydrogen halide while the reaction mixture is maintained at below room temperature, i.e. 0°-15° C. Pyridine or dimethylanilien hydrogen halide forms a precipitate which can be removed by filtration upon completion of the reaction. In this fashion, refluxing of the mixture during reaction is obviated. Recovery of the silane is achieved by distillation in the same fashion as described above.

In conformity with the generic formula of the subject silanes, the halosilane reactant is a ($C_1$-$C_5$ alkyl) halosilane, a ($C_2$-$C_4$ alkenyl) halosilane or a tetrahalosilane. Preferably the halogen is chlorine. The phenoxy -$C_1$-$C_4$ alkanol has the general formula

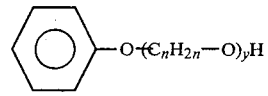

wherein y and n are defined as above in the silane formula. Illustrative examples of useful halosilanes include tetrachlorosilanes, methyltrichlorosilane, methyltribromosilane, ethyltrichlorosilane, propyltrichlorosilane, n-butyltrichlorosilane, n-amyltrichlorosilane, vinyltrichlorosilane, allyltrichlorosilane, butenyltrichlorosilane and the like. Useful phenoxyalkanols include phenoxymethanol, 2-phenoxyethanol, 3-phenoxypropanol-1, 4-phenoxybutanol-1, 1-methyl-2-phenoxyethanol, 1-methyl-3-phenoxypropanol-1, phenoxyethoxyethanol, phenoxydiethoxyethanol and the like and mixtures thereof. Some of these alcohols may also be described as phenyl ethers of ethylene glycol, trimethylene glycol, tetramethylene glycol, propylene glycol and n-butylene glycol.

In preparing the preferred silanes, the 2-phenoxyethanol employed often contains small quantities of phenoxyethoxyethanol and phenoxydiethoxyethanol which results in a product containing small amounts of the silanes corresponding to these ethoxyethanols. Those skilled in the art will appreciate that as used herein the term phenoxy- $C_1$-$C_4$ alkanol is meant to include phenoxyalkanols containing small quantities of the alkoxy and diethoxy homologues.

The following examples will serve to illustrate the subject invention.

EXAMPLE 1

Vinyl tris (2-phenoxyethoxy) silane was prepared by the following reaction:

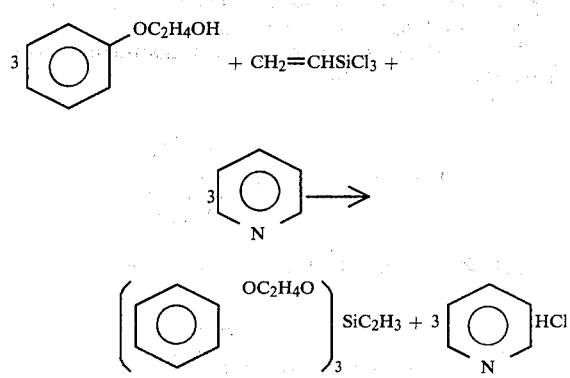

Into a liter, round bottomed flask, equipped with condenser, thermometer, mechanical stirrer and dropping funnel, protected from atmospheric moisture, were placed 0.6 mole phenyl cellosolve (also known as 2-phenoxyethanol), 0.65 mole of dry pyridine and 300 ml of toluene. The flask was cooled to 5° C. and a mixture of 0.2 mole of vinyltrichlorosilane in 100 ml of toluene was added dropwise, always maintaining a pot temperature of less than 15° C. When the addition was complete, the flask was allowed to reach room temperature and was so maintained for 4 hours.

The precipitate of pyridine hydrochloride was filtered and washed with toluene. The toluene containing the product was removed under vacuum in a rotatory evaporator.

The residual product was distilled at 254°–56° C. and 0.8 mmHg. The yield was 82.64%. The material recovered was identified as vinyl tris (2-phenoxyethoxy) silane by infrared spectroscopy.

EXAMPLE 2

Methyl tris (2-phenoxyethoxy) silane was prepared by the following reaction:

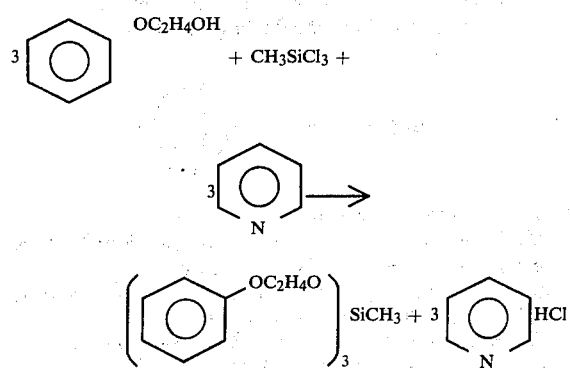

In the apparatus described in Example 1 were added 0.75 mole of phenyl cellosolve, 0.80 mole dry pyridine and 400 ml dry toluene. The flask was cooled to 5° C. and from a dropping funnel was added slowly a mixture of 0.25 mole of methyltrichlorosilane in 100 ml of toluene. The temperature was kept below 10° C. throughout the addition. The flask was then allowed to come to room temperature and so kept for 3 hours.

The white precipitate of pyridine hydrochloride was removed from the solution by filtration and the toluene was removed under vacuum in a rotatory evaporator. The product was purified by distillation at 256°–8° and at 1 mmHg. The yield was 80%. The material recovered was identified as methyl tris (2 phenoxyethoxy) silane by infrared spectroscopy.

EXAMPLE 3

The water tree and the electrical tree retardant properties of the silanes prepared in Examples 1 and 2 were evaluated in a series of accelerated tests.

The sample compositions were prepared by milling a commercial grade of polyethylene and a small quantity of the treeing additive being evaluated on a 2-roll mill at about 300° F. for about 10 minutes to obtain a homogeneous dispersion. The crepe obtained was then used to prepare the samples for electric tree and water tree testing using the procedures described below. All the compositions comprised a commercial grade of polyethylene having a Melt Index of about 0.20 to 0.35 g/10 min. and a density of about 0.917 grams/cubic centimeter (g/cc) and contained the "treeing" additive in the amount reported in the test results of Table I. The control sample did not contain a "treeing" additive.

In order to determine the utility and effectivness of the polymeric compositions containing the silanes of present invention with regard to its inhibiting effect on the water treeing and the electrical treeing thereof, the compositions were evaluated by the use of accelerated tests.

The electrical tree tests were performed using a method similar to ASTM 3756. Strips of the test material approximately 1" wide were cut from a ¼" thick compression molded plaque. The block was machined to give a strip having parallel edges 1" apart. The strip was then cut into 1" square blocks. A blunt needle and a sharp needle were inserted into opposite parallel edges, at elevated temperatures, so that the points were ⅛" apart. Needle insertion and cooling of the sample was performed slowly to avoid inducing thermal or mechanical stresses in the specimen. The sharp needle had a tip diameter of about 0.0002" while the diameter of the blunt needle was 0.002". Eight specimens were prepared and tested simultaneously for each composition. The electrical tree test was performed by energizing the sharp needle at 15 KV using a frequency of 60 Hz; the blunt needle was connected to ground. The time required for each of the eight specimens to fail by tree growth and subsequent electrical short was recorded. The time required for 50% of the samples to fail was employed to characterize the effectiveness of the tree retardant being evaluated.

The water tree test was performed using a procedure similar to that described in U.S. Pat. No. 4,144,202. A compression molded disc about 150 millimeters (mm.) in diameter having 10 conical depressions was prepared for each composition. The geometry of the disc and dimensions of the depressions are substantially the same as shown in U.S. Pat. No. 4,144,202. The base of the disc was sprayed with silver paint which served as the ground electrode. An acrylic tube 6" long was clamped to the upper face forming a test cell. About 150 ml. of 0.01 N sodium chloride solution was poured into the cell and the air bubbles trapped on the surface of the sample were removed. A platinum wire ring was then immersed in the electrolyte and connected to an electrical supply which provided 5 KV at a frequency of 3 KHz. Samples were energized for 22 hours after which time they were removed from the test cell and washed with distilled water. The ten depressions were cut from the disc and stained to make the water trees more visible. Thin sections were obtained with a microtome, which were then examined microscopically (at 200×) and the tree size measured. Normally four discs were made for each sample so that the average tree size was calculated from forty individual measurements. In evaluating different tree retardants, the relative tree size was determined by comparing the average tree size obtained on a standard thermoplastic high voltage insulation material containing no tree retardant additives.

All parts and percentages are by weight and temperatures in degrees Fahrenheit unless otherwise noted.

The results of the electrical tree and water tree testing are shown in Table I.

TABLE I

| Treeing Additive | Additive Amount, % | Double Needle Test Time to 50% Failure (minutes) | Water Tree Test (Relative Tree Size) |
|---|---|---|---|
| Control (no additive) | — | 75 | 1.00 |
| Vinyl-tris (2-phenoxy-ethoxy) silane | 1.5 | 6000 | 0.22 |
| Methyl-tris (2-phenoxy-ethoxy) silane | 1.0 | 300 | 0.27 |

What is claimed is:

1. A composition of matter comprising a compound corresponding to the formula

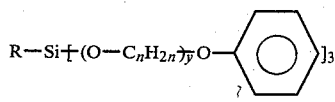

wherein
R is $C_1$–$C_5$ alkyl, $C_2$–$C_4$ alkenyl or

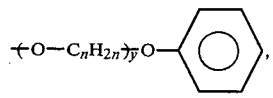

y is an integer of 1 to 5 and n is an integer of 1 to 4.

2. A composition of matter according to claim 1 wherein R is methyl, y is 1 and n is 2.
3. A composition of matter according to claim 1 wherein R is vinyl, y is 1 and n is 2.
4. A composition of matter according to claim 1 wherein R is ethyl, y is 1 and n is 2.
5. A composition of matter according to claim 1 wherein R is methyl, y is 1 and n is 3.
6. A composition of matter according to claim 1 wherein R is vinyl, y is 1 and n is 3.
7. A composition of matter according to claim 1 wherein R is

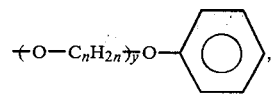

y is 1 and n 2.
8. A composition of matter according to claim 1 wherein R is vinyl, y is 2 and n is 2.
9. A composition of matter according to claim 1 wherein R is vinyl, y is 3 and n is 2.
10. A process for preparing an organosilane corresponding to the formula

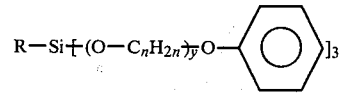

wherein R is $C_1$–$C_5$ alkyl, $C_2$–$C_4$ alkenyl or

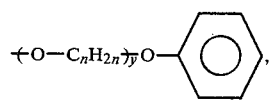

y is an integer of 1 to 5 and n is an integer of 1 to 4 which comprises:
(a) reacting together an alcohol having the formula:

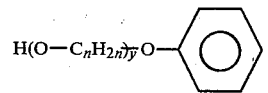

with a halosilane having the formula ($C_1$–$C_5$ alkyl) Si $X_3$ when R is $C_1$–$C_5$ alkyl, ($C_2$–$C_4$ alkenyl) Si $X_3$ when R is $C_2$–$C_4$ alkenyl or Si $X_4$ when R is

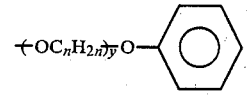

wherein X is a halogen and n and y have the meanings given above in the presence of a hydrogen halide acceptor and an inert solvent,
(b) separating the hydrogen halide acceptor containing hydrogen halide from the reaction mixture,
(c) isolating a compound having the formula

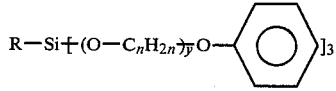

from the reaction mixture.
11. A process according to claim 10 wherein R is methyl, y is 1, n is 2 and X is chloride.
12. A process according to claim 10 wherein R is vinyl, y is 1, n is 2 and X is chloride.
13. A process according to claim 10 wherein R is vinyl, y is 2, n is 2 and X is chloride.
14. A process according to claim 10 wherein the hydrogen halide acceptor is pyridine or dimethylaniline.

* * * * *